(12) United States Patent
Saha

(10) Patent No.: US 10,775,457 B2
(45) Date of Patent: Sep. 15, 2020

(54) RF SHIELD FOR REDUCING EDDY CURRENT IN A PET-MR IMAGING SYSTEM

(71) Applicant: GE Precision Healthcare LLC, Wauwatosa, WI (US)

(72) Inventor: Saikat Saha, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 239 days.

(21) Appl. No.: 15/852,735

(22) Filed: Dec. 22, 2017

(65) Prior Publication Data

US 2018/0120395 A1    May 3, 2018

Related U.S. Application Data

(62) Division of application No. 13/927,617, filed on Jun. 26, 2013, now abandoned.

(51) Int. Cl.
  *G01R 33/422*  (2006.01)
  *G01R 33/48*   (2006.01)
  *A61B 6/03*    (2006.01)
  *A61B 6/00*    (2006.01)
  *A61B 5/055*   (2006.01)
  (Continued)

(52) U.S. Cl.
   CPC .......... *G01R 33/422* (2013.01); *A61B 5/0035* (2013.01); *A61B 5/055* (2013.01); *A61B 6/037* (2013.01); *A61B 6/4258* (2013.01); *A61B 6/4275* (2013.01); *A61B 6/4417* (2013.01); *G01R 33/481* (2013.01); *G01R 33/56518* (2013.01)

(58) Field of Classification Search
   CPC ..... A61B 5/055; A61B 5/0035; A61B 6/4258; A61B 6/4275; A61B 6/4417; A61B 6/037; G01R 33/22; G01R 33/422; G01R 33/481; G01R 33/56518
   See application file for complete search history.

(56) References Cited

U.S. PATENT DOCUMENTS

| | | | |
|---|---|---|---|
| 7,728,590 B2 | 6/2010 | Eberler et al. | |
| 2011/0025329 A1* | 2/2011 | Utturkar | G01R 33/3403 324/318 |
| 2012/0062231 A1 | 3/2012 | Saha et al. | |

(Continued)

OTHER PUBLICATIONS

Peng et al. 2010 Phys. Med. Biol. 55:265-280.

*Primary Examiner* — Keith M Raymond
*Assistant Examiner* — Patrick M Mehl
(74) *Attorney, Agent, or Firm* — Armstrong Teasdale LLP

(57) ABSTRACT

An imaging apparatus is disclosed that includes an MRI system, either as a stand-alone system or hybrid PET-MRI system. The MRI system includes gradient coils positioned about a patient bore, an RF coil former comprising an inner surface and an outer surface, an RF shield positioned on the outer surface of the RF coil former so as to be formed about the RF coil former, and an RF coil positioned on the inner surface of the RF coil former and about the patient bore, with the RF coil coupled to a pulse generator to emit an RF pulse sequence and receive resulting MR signals from a subject of interest. The RF shield includes a plurality of slits formed therein configured to disrupt the formation of gradient field induced eddy currents on the RF shield, so as to prevent the generation of high temperature profiles on the surface of the shield.

15 Claims, 7 Drawing Sheets

(51) Int. Cl.
  *A61B 5/00* (2006.01)
  *G01R 33/565* (2006.01)

(56) References Cited

U.S. PATENT DOCUMENTS

| | | | |
|---|---|---|---|
| 2012/0229141 A1* | 9/2012 | Brown | G01R 33/422 |
| | | | 324/322 |
| 2012/0293173 A1 | 11/2012 | de Lima et al. | |
| 2013/0293232 A1* | 11/2013 | Boskamp | G01R 33/422 |
| | | | 324/318 |

* cited by examiner

RF SHIELD FOR REDUCING EDDY CURRENT IN A PET-MR IMAGING SYSTEM

CROSS-REFERENCE TO RELATED APPLICATIONS

This application is a divisional of U.S. patent application Ser. No. 13/927,617, filed on Jun. 26, 2013, the disclosure of which is incorporated herein by reference in its entirety.

BACKGROUND

Embodiments of the invention relate generally to magnetic resonance (MR) imaging, and more specifically, to an RF shield configured to prevent the generation of high temperature profiles on the surface thereof resulting from eddy current heating, so as to minimize impact on the performance of thermally sensitive parts, such as a positron emission tomography (PET) detector array in a hybrid PET-MRI system.

MR imaging involves the use of magnetic fields and excitation pulses to detect the free induction decay of nuclei having net spins. When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a RF magnetic field (excitation field $B_1$) which is in the x-y plane, i.e. perpendicular to the DC magnetic field (B0) direction, and which is near the Larmor frequency, the net aligned moment, or "longitudinal magnetization", $M_Z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well-known reconstruction techniques.

PET imaging involves the creation of tomographic images of positron emitting radionuclides in a subject of interest. A radionuclide-labeled agent is administered to a subject positioned within a detector ring. As the radionuclides decay, positively charged particles known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV.

It is these gamma rays that are detected by the scintillators of the detector ring. When struck by a gamma ray, each scintillator illuminates, activating a photovoltaic component, such as a photodiode. The signals from the photovoltaics are processed as incidences of gamma rays. When two gamma rays strike oppositely positioned scintillators at approximately the same time, a coincidence is registered. Data sorting units process the coincidences to determine which are true coincidence events and sort out data representing deadtimes and single gamma ray detections. The coincidence events are binned and integrated to form frames of PET data which may be reconstructed into images depicting the distribution of the radionuclide-labeled agent and/or metabolites thereof in the subject.

In combination PET-MRI systems, the RF shield associated with the MRI scanner is positioned in between the RF body coil and the gradient coil to help prevent the high amplitude RF field being radiated out, with the PET detector array being placed outside the RF shield in order to shield the sensitive detector array from the RF field. Depending on the proximity of the RF shield to the gradient coil and the type of gradient pulsing sequence applied, large amount of eddy-currents are created on the RF shield surface, with the pattern of these eddy current more or less mirroring the primary gradient current pattern. The eddy current generated on the RF shield produces heat that create high temperature profiles that affect the performance of any thermally sensitive parts located on or near the RF shield, such as the PET detector modules. The eddy current generated on the RF shield also raises the overall temperature of the patient bore, which may potentially cause discomfort to a subject being imaged.

It would therefore be desirable to provide an RF shield that prevents the generation of high temperature profiles on the surface of the RF shield resulting from eddy current heating, such as by disrupting larger eddy current profiles and any azimuthal generation of eddy current and by preventing the build-up of axial currents on the shield. It would also be desirable for the RF shield to still provide the necessary amount of shielding to the PET detector array and maintain the RF coil performance and image quality.

BRIEF DESCRIPTION

Embodiments of the invention provide an RF shield for use in a stand-alone or hybrid MRI system.

In accordance with one aspect of the invention, an imaging apparatus includes a MRI system comprising a plurality of gradient coils positioned about a patient bore, an RF coil former comprising an inner surface and an outer surface, an RF shield positioned on the outer surface of the RF coil former so as to be formed about the RF coil former, and an RF coil positioned on the inner surface of the RF coil former and about the patient bore, with the RF coil coupled to a pulse generator to emit an RF pulse sequence and receive resulting MR signals from a subject of interest. The RF shield includes a plurality of slits formed therein configured to disrupt the formation of gradient field induced eddy currents on the RF shield.

In accordance with another aspect of the invention, an RF coil assembly for use in a stand-alone or hybrid MRI system includes a generally cylindrical RF coil former having an inner surface and an outer surface, an RF shield affixed to the outer surface of the RF coil former and configured to conform to the outer surface thereof, and an RF coil affixed to an inward facing surface of the RF coil former. The RF shield of the RF coil assembly further includes a plurality of longitudinal slits cut in the RF shield extending in a z-direction along the RF shield and a plurality of circumferential slits cut in the RF shield extending in a circumferential direction along the RF shield, wherein the plurality of longitudinal slits and the plurality of circumferential slits are configured to disrupt the formation of gradient field induced eddy currents on the RF shield, so as to thereby reduce a surface temperature of the RF shield.

In accordance with yet another aspect of the invention, a PET-MRI apparatus includes a MRI system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest. The PET-MRI apparatus also includes a positron emission tomography (PET) system having a detector array positioned to encircle the bore, with the detector array being controlled to acquire PET emissions of the subject of interest. The RF shield or the MRI system further includes a pair of raised portions formed on opposing ends of the RF shield, an indented portion formed between the pair of raised portions that is indented in the radial direction inwardly toward the patient bore, a plurality of longitudinal slits formed in the RF shield and extending in a z-direction along the RF shield, and a plurality of circumferential slits formed in the RF shield and extending in a circumferential direction along the RF shield.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

An RF coil assembly is provided that includes an RF shield having a plurality of slits formed therein that are configured to prevent the generation of high temperature profiles on the surface of the RF shield. Longitudinal slits and/or circumferential slits are formed in the RF shield that disrupt the formation of eddy currents on the RF shield surface, so as to reduce the heat produced from such eddy currents and prevent the generation of the high temperature profiles that affect the performance of any thermally sensitive parts located on or near the RF shield, such as PET detector modules.

According to embodiments of the invention, the RF coil assembly can be implemented in a variety of imaging systems or apparatuses. For example, the RF coil assembly can be incorporated into a stand-alone MR imaging system or can be incorporated into a hybrid MR imaging system, such as a hybrid PET-MR imaging system, for example. Thus, while embodiments of the invention are set forth here below with respect to a hybrid PET-MR imaging system, it is recognized that other stand-alone and hybrid MR imaging systems are considered to be within the scope of the invention.

Figure 1:
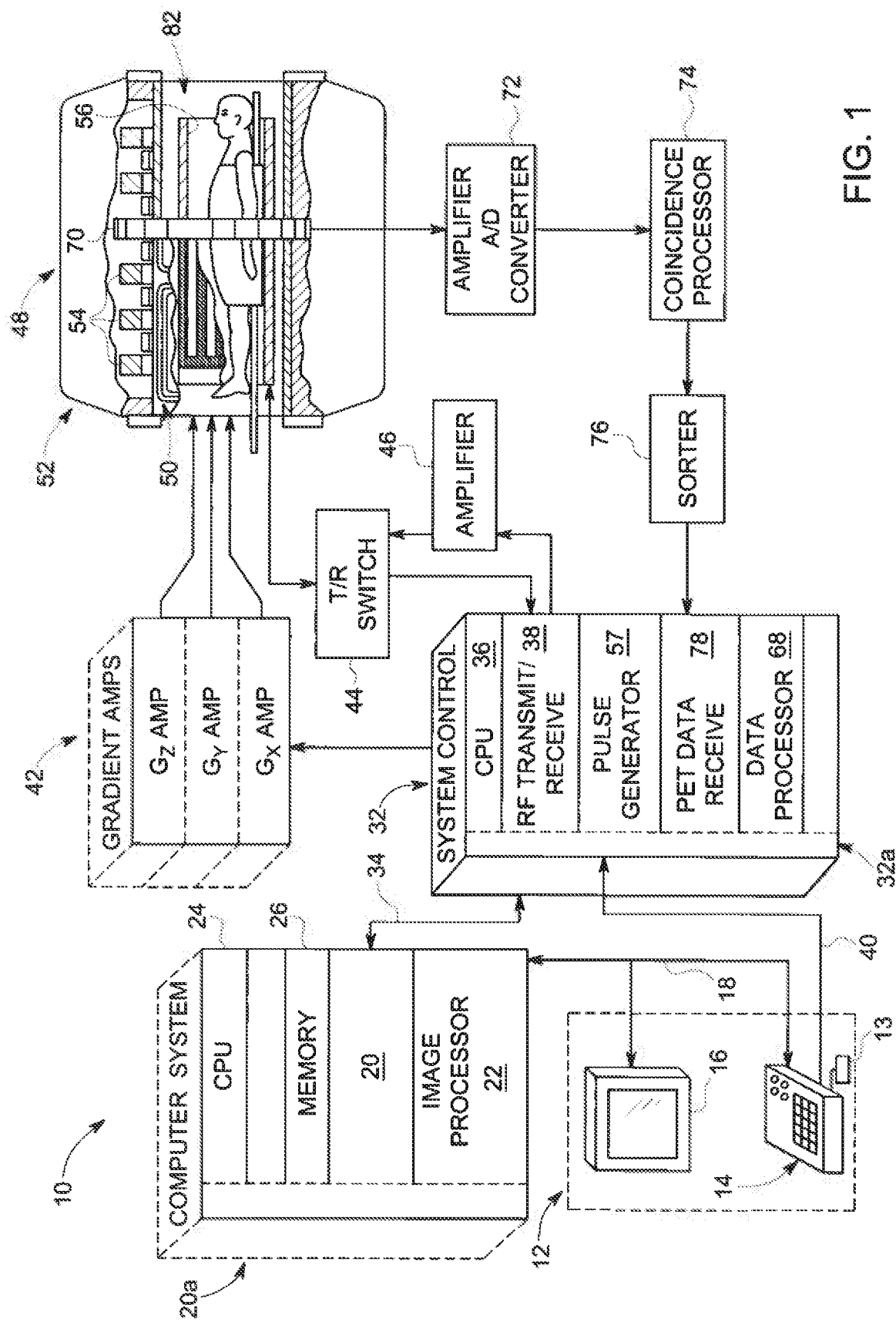
FIG. 1 is a schematic block diagram of an exemplary PET-MR imaging system for use with an embodiment of the invention.

Referring to FIG. 1, the major components of an exemplary hybrid PET-MR imaging system 10 that may incorporate embodiments of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules, such as an image processor module 22, a CPU module 24 and a memory module 26. The computer system 20 may also be connected to permanent or back-up memory storage, a network, or may communicate with a separate system control 32 through link 34. The input device 13 can include a mouse, keyboard, track ball, touch activated screen, light wand, or any similar or equivalent input device, and may be used for interactive geometry prescription.

The system control 32 includes a set of modules in communication with one another and connected to the operator console 12 through link 40. It is through link 34 that the system control 32 receives commands to indicate the scan sequence or sequences that are to be performed. For MR data acquisition, an RF transmit/receive module 38 commands the scanner 48 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 44 and amplifier 46 control the flow of data to scanner 48 from RF transmit module 38 and from scanner 48 to RF receive module 38. The system control 32 also connects to a set of gradient amplifiers 42, to indicate the timing and shape of the gradient pulses that are produced during the scan.

The gradient waveform instructions produced by system control 32 are sent to the gradient amplifier system 42 having Gx, Gy, and Gz amplifiers. Amplifiers 42 may be external of scanner 48 or system control 32, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil 56 (i.e., whole-body RF coil). Alternatively, the gradient coils of gradient coil assembly 50 may be independent of the magnet assembly 52. The coils 56 of the RF coil may be configured for both transmitting and receiving, or for transmit-only or receive-only. A pulse generator 57 may be integrated into system control 32 as shown, or may be integrated into scanner equipment 48, to produce pulse sequences or pulse sequence signals for the gradient amplifiers 42 and/or the RF coil 56. In addition, pulse generator 57 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 56 or by separate receive coils and are then transmitted to the RF transmit/receive module 38 via T/R switch 44. The MR signals are demodulated, filtered, and digitized in the data processing section 68 of the system control 32.

An MR scan is complete when one or more sets of raw k-space data has been acquired in the data processor 68. This raw k-space data is reconstructed in data processor 68 which operates to transform the data (through Fourier or other techniques) into image data. This image data is conveyed through link 34 to the computer system 20 where it is stored in memory 26. Alternatively, in some systems computer system 20 may assume the image data reconstruction and other functions of data processor 68. In response to commands received from the operator console 12, the image data stored in memory 26 may be archived in long term storage or may be further processed by the image processor 22 or CPU 24 and conveyed to the operator console 12 and presented on the display 16.

In combined MR-PET scanning systems, PET data may be acquired simultaneously with the MR data acquisition described above. Thus, scanner 48 also contains a positron emission detector array or ring 70, configured to detect gamma rays from positron annihilation radiations emitted from a subject. Detector array 70 preferably includes a plurality of scintillators and photovoltaics arranged about a gantry. Detector array 70 may, however, be of any suitable construction for acquiring PET data. In addition, the scintillator packs, photovoltaics, and other electronics of the detector array 70 are shielded from the magnetic fields and/or RF fields applied by the MR components 54, 56 by way of an RF shield (not shown), as will be explained in detail below.

Gamma ray incidences detected by detector array 70 are transformed, by the photovoltaics of the detector array 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 26 for subsequent processing 68. PET images may then be reconstructed by image processor 22 and may be combined with MR images to produce hybrid structural and metabolic or functional images. Conditioning circuits 72, coincidence processor 74 and sorter 76 may each be external of scanner 48 or system control 32, or may be integrated therein.

Figure 2:
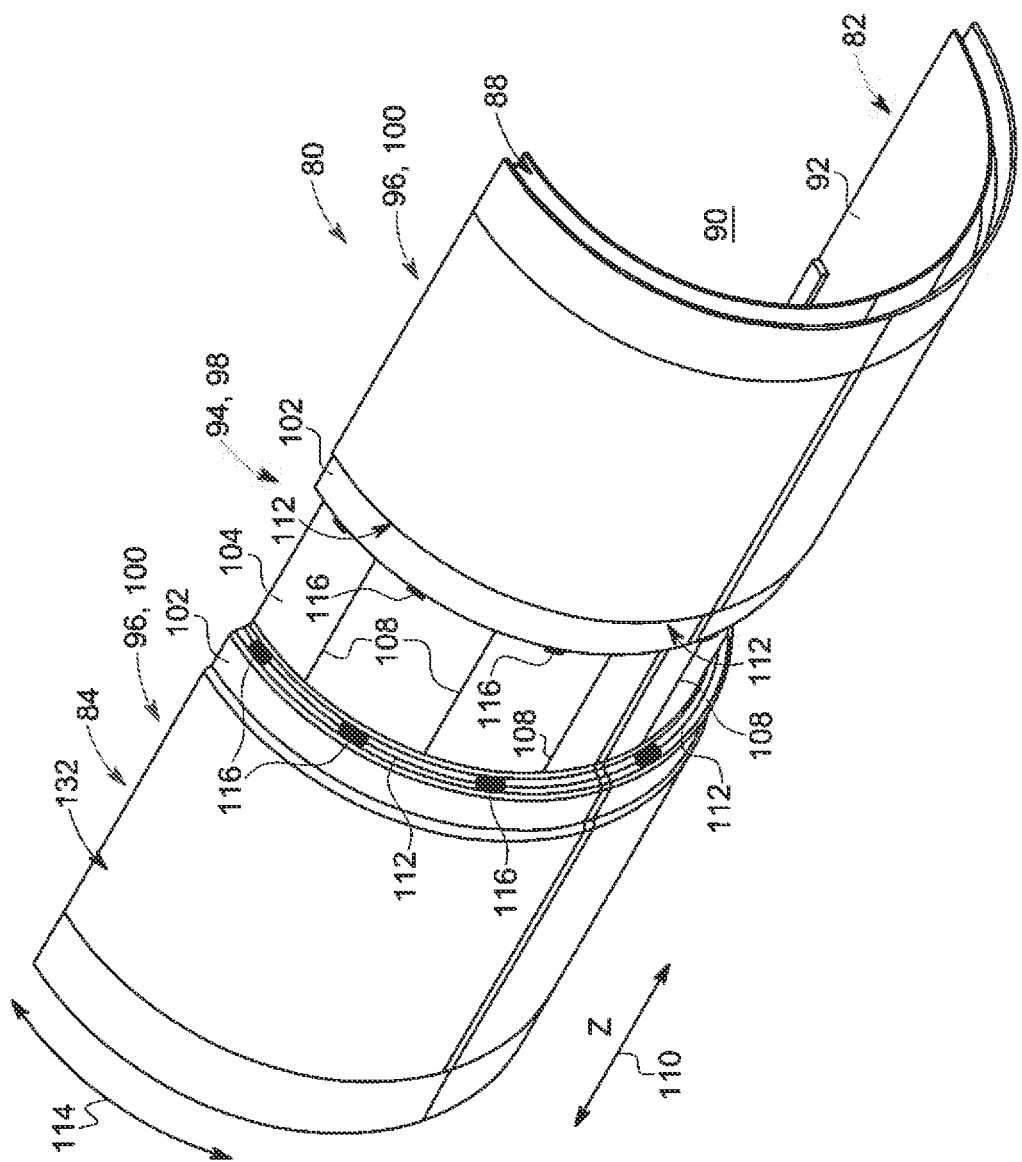
FIGS. 2 and 3 are perspective views of an RF coil assembly, including an RF shield, for use in the PET-MR imaging system of FIG. 1 according to an embodiment of the invention.
Figure 3:
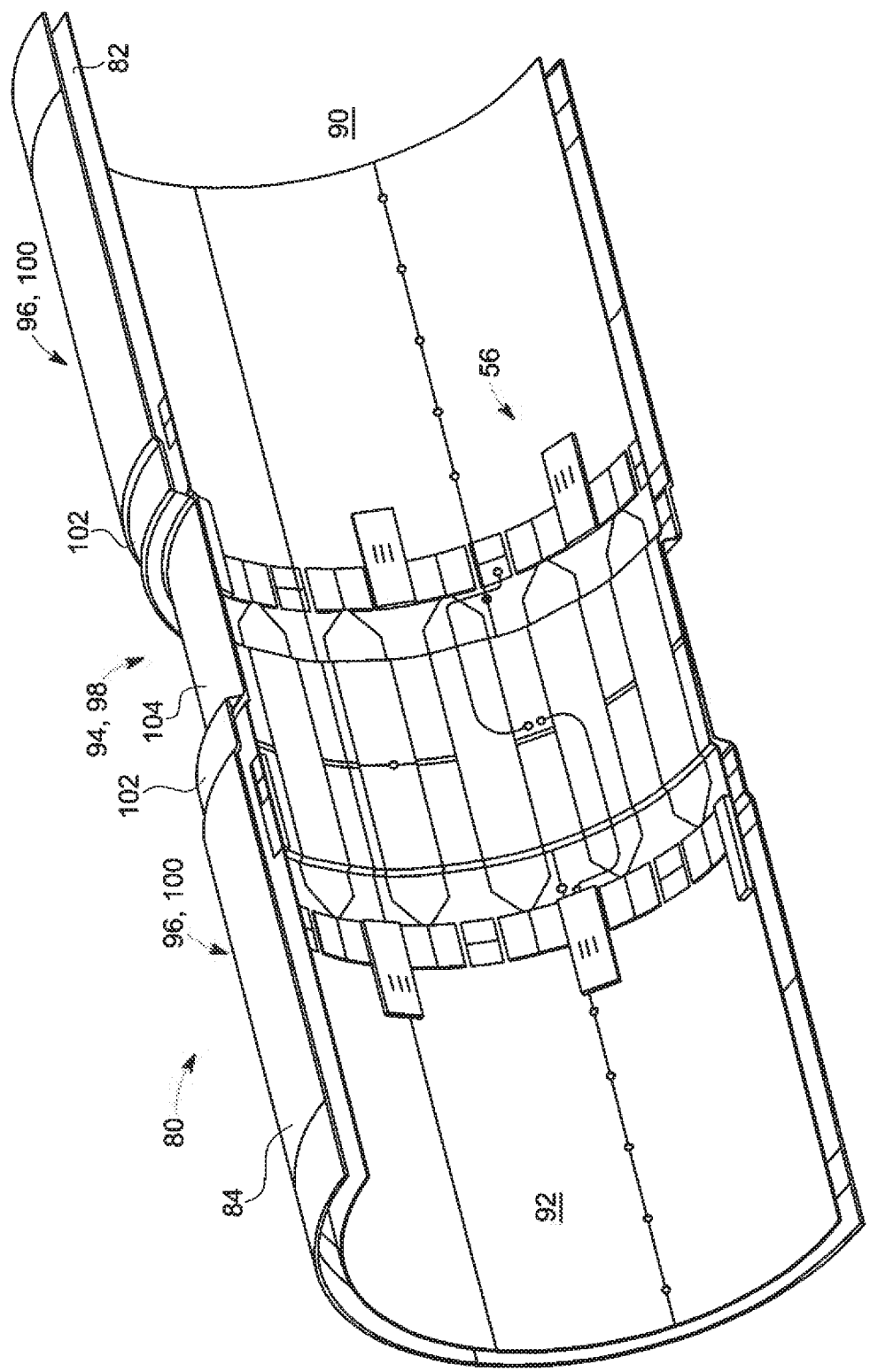

Referring now to FIGS. 2 and 3, an RF coil assembly 80 that is included in the hybrid PET-MR imaging system 10 is shown, although it is recognized that RF coil assembly 80 could also be implemented for use in other stand-alone MRI systems or other hybrid MRI systems. The RF coil assembly 80 includes an RF coil former or tube 82, an RF shield 84, and the RF body coil 56. According to an embodiment of the invention, the RF shield 84 is formed of stainless steel mesh and the RF coil former 82 is composed of fiberglass or fiber reinforced plastic (FRP) cylinders on the radially inner and radially outer surfaces, with a foam material sandwiched between the inner and outer surfaces, although it is recognized that other suitable materials could also be used. The RF shield 84 is positioned on the outer surface 88 of RF coil former 82 and is formed there about. The RF coil 56 is formed on an inner surface 92 of RF coil former 82 with an annular receiving or imaging area 90 (i.e., patient bore), and is separated radially from gradient coils 50 by RF shield 84, with the RF shield 84 functioning to de-couple the RF coils 56 from the gradient coils 50 (FIG. 1) in the PET-MR imaging system 10.

As shown in FIG. 2, the RF coil former 82 is generally cylindrical in shape but includes an indentation or indented portion 94 formed therein in a radial direction and in an area that corresponds to the PET detector array 70 (FIG. 1) of the PET-MR imaging system 10. Thus, the indented portion 94 will be formed in a generally central area lengthwise on the RF coil former 82, with a pair of raised or stepped-up portions 96 of the RF coil former 82 being formed on opposing sides of the indented portion 94 and at opposing ends of the RF coil former 82. The RF shield 84 is applied over the outer surface 88 of RF coil former 82 and conforms to the RF coil former 82, such that the RF shield 84 has an identical shape as the outer surface 88 of the RF coil former 82. The RF shield 84 thus also includes an indentation/indented portion 98 formed therein in the area that corresponds to the PET detector array 70 (FIG. 1), with the indented portion 98 being between raised portions 100 of the RF shield 84.

Figure 4:
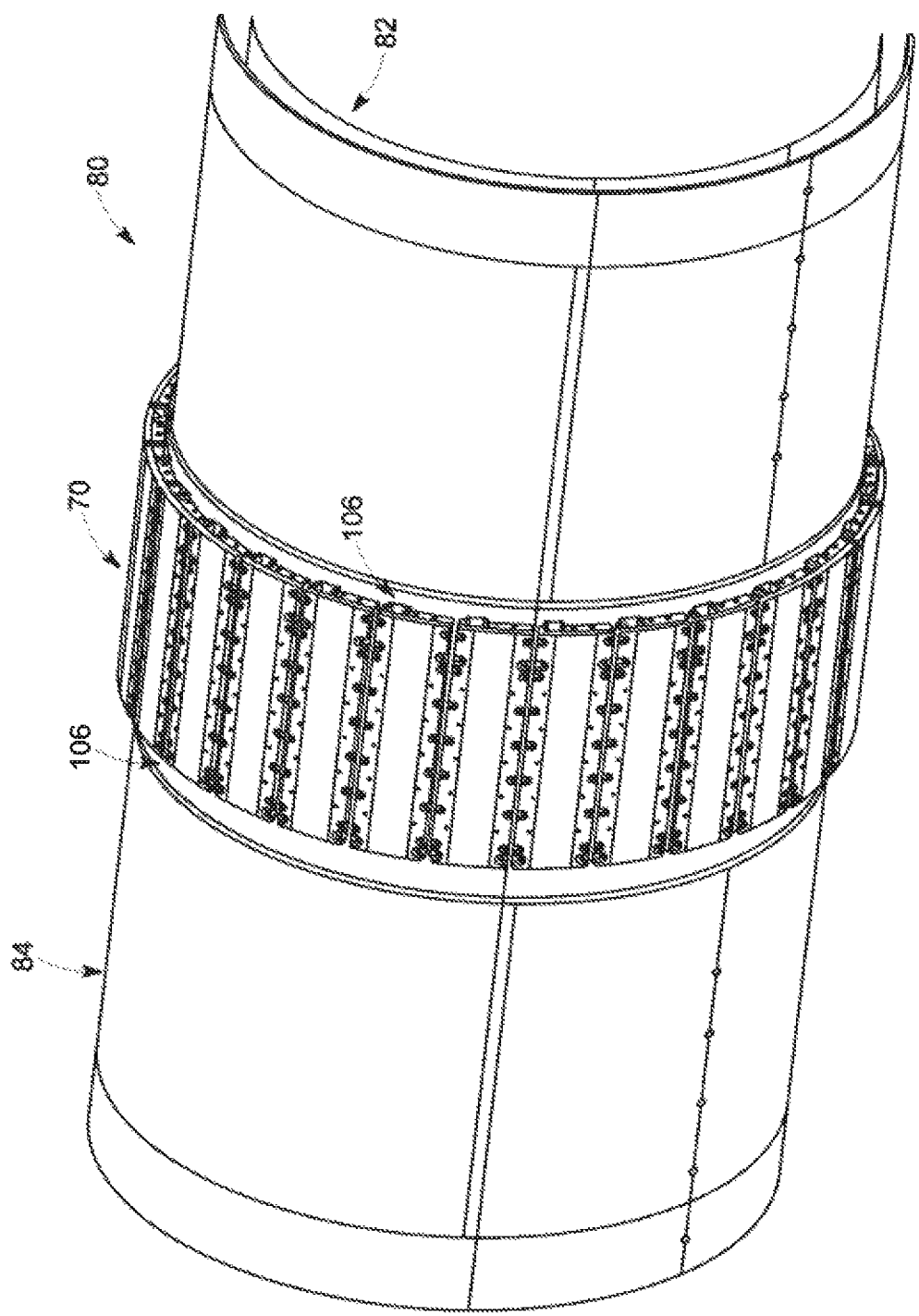
FIG. 4 is a perspective view of the RF coil assembly of FIGS. 2 and 3 with a PET detector array positioned on the RF shield according to an embodiment of the invention.

According to an exemplary embodiment of the invention, the indented portions 94, 98 in RF coil former 82 and RF shield 84 have a stepped configuration. As shown in FIG. 2, a first step 102 and a second step 104 are formed in the indented portions 94, 98 of RF coil former 82 and RF shield 84, with the second step 104 being further indented from raised portions 96, 100 of the RF coil former 82 and RF shield 84 than the first step 102. The first and second steps 102, 104 accommodate positioning of the detector array 70 and an accompanying mechanical support frame 106 therein, as shown in FIG. 4. That is, mechanical support frame 106 can be positioned on first step 102 of the indented portions 94, 98, such that an outer surface of the support frame is flush with the raised portions 100 of the RF shield 84. Similarly, detector array 70 may be positioned on second step 104 of the indented portions 94, 98, such that the detector array is flush with the raised portions 100 of the RF shield 84.

As shown in FIG. 2, according to one embodiment of the invention, longitudinal slits 108 are cut/formed in RF shield 84 extending in the z-direction 110. The slits 108 may be formed to have a width of 1 mm, for example, and are configured to reduce heating caused by gradient field induced eddy currents in the RF shield 84 during operation of the PET-MR imaging system 10 by increasing impedance for the gradient eddy currents due to increased path length. That is, the longitudinal slits along the z-axis of the RF shield 84 are strategically cut to disrupt the larger eddy current profiles and prevent any azimuthal generation of eddy current. According to the embodiment of FIG. 2, the slits 108 are formed in the indented portion 98 of RF shield 84—and more specifically in the region of the indented portion 98 that accommodates the detector array 70, i.e., in the region of second step 104.

As further shown in FIG. 2, in addition to the longitudinal slits 108 formed in RF shield 84, circumferential slits 112 are also strategically cut/formed in the RF shield 84. The circumferential slits 112 extend in a circumferential direction 114 along the RF shield 84 and function to prevent the build-up of axial currents on the shield. According to the embodiment of FIG. 2, circumferential slits 112 are formed in the RF shield 84 between the indented portion 98 of the shield and the raised portions 100. The gap between the raised portions 100 of the RF shield and the indented portion 98 formed by the circumferential slits 112 are bridged by capacitive devices 116 that act as an RF short, so as to minimize heat generation on the RF shield 84 and hence the temperature rise thereof. According to embodiments of the invention, the capacitive devices 116 may be provided as disc capacitors, jumpers, dielectric double layered PCB capacitors, or lumped capacitors, for example.

Figure 5:
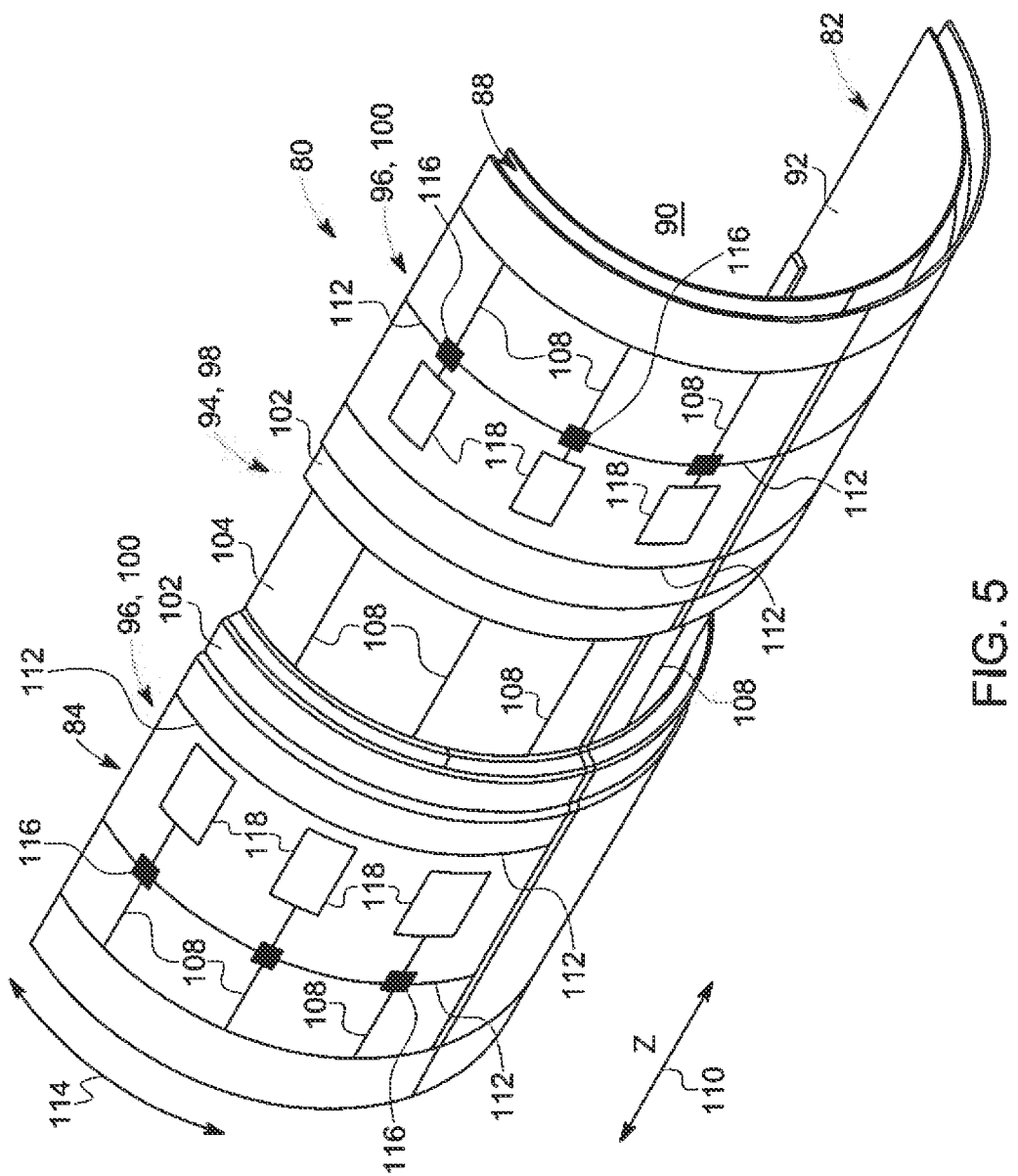
FIG. 5 is a perspective view of an RF coil assembly, including an RF shield, for use in the PET-MR imaging system of FIG. 1 according to another embodiment of the invention.

Referring now to FIG. 5, the RF shield 84 is shown according to another embodiment of the invention. In the embodiment shown in FIG. 5, longitudinal slits 108 are formed in RF shield 84 extending in the z-direction, with the longitudinal slits 108 being formed both in the indented portion 98 of RF shield 84 (i.e., in the region of second step 104) and in the raised portions 100 of RF shield 84. The slits 108 may be formed to have a width of 1 mm, for example, and are configured to reduce heating caused by gradient field induced eddy currents in the RF shield 84 during operation of the PET-MR imaging system 10 by increasing impedance for the gradient eddy currents due to increased path length.

Figure 6A:
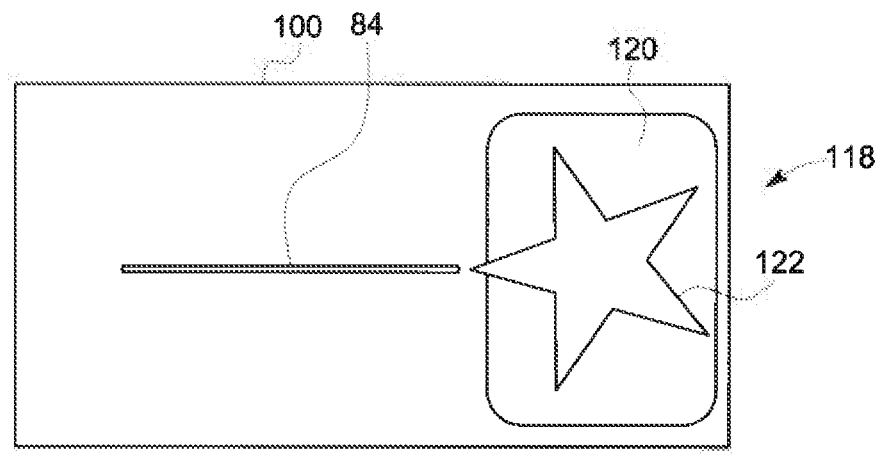
FIGS. 6A and 6B are views of heat removal devices for use with the RF shield of FIG. 5 according to embodiments of the invention.
Figure 6B:
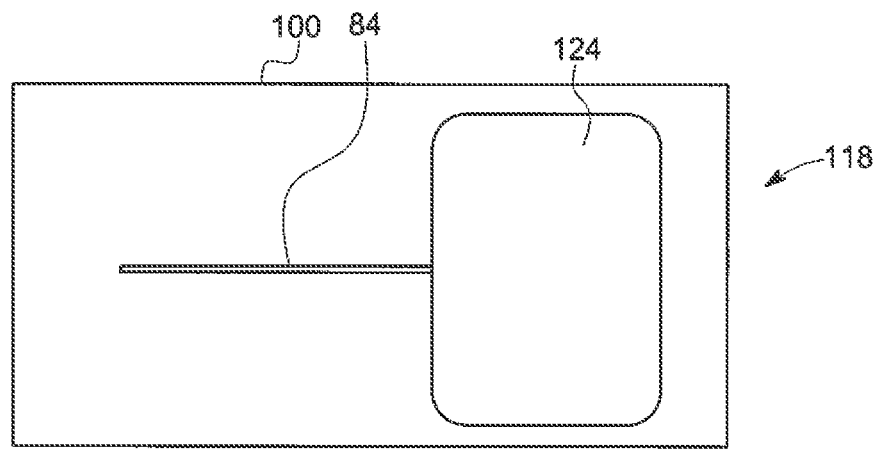

According to an exemplary embodiment, the slits 108 are formed in an outer region of each of raised portions 100 of RF shield 84, with a heat removal device 118 being positioned on the RF shield 84 at an end of a respective longitudinal slit 108 on raised portions 100 to remove heat therefrom. According to embodiments of the invention, the heat removal device 118 includes electrically insulating and thermally conductive elements that may either be integrated into a single component or formed as separate components. For example, referring to FIGS. 6A and 6B, various embodiments of heat removal devices 118 are shown. In the embodiment of FIG. 6A, the heat removal device 118 includes an electrically insulating base plate 120 affixed to the RF shield 84 (i.e., on raised portion 100 of the shield) at the end of longitudinal slit 108, with a thermally conductive plate 122 that exhibits high thermal conductivity being positioned on the electrically insulating base plate 120 and adjacent the end of longitudinal slit 108. In the embodiment of FIG. 6B, the heat removal device 118 is formed of a single heat spreader 124 formed of a material that exhibits poor electrical conductivity and high thermal conductivity, with the heat spreader 124 being affixed to the RF shield 84 (i.e., on raised portion 100 of the shield) at the end of longitudinal slit 108. It is recognized that the shape, size, and location of the heat removal devices 118 can be varied and optimized to achieve a desired level of heat removal/performance.

Referring again to FIG. 5, the embodiment of the RF shield 84 shown therein also includes circumferential slits 112 cut/formed in the RF shield 84. More specifically, the circumferential slits 112 are cut/formed in the raised portions 100 of RF shield 84 so as to extend in a circumferential direction 114 along the RF shield 84, with the slits 112 functioning to prevent the build-up of axial currents on the shield. As further shown in FIG. 5, capacitive devices 116 can be positioned at desired locations on raised portions 100 of the RF shield to bridge the circumferential slits 112 to act as an RF short and thereby minimize heat generation on the RF shield 84 and the temperature rise thereof. According to embodiments of the invention, the capacitive devices 116 may be provided as disc capacitors, jumpers, dielectric double layered PCB capacitors, or lumped capacitors, for example.

While a number of embodiments of an RF shield 84 have been shown and described here above, it is recognized that various other arrangements and configurations of longitudinal and circumferential slits 108, 112 are considered to be within the scope of the invention. That is, it is recognized that the specific location and width of the slits 108, 112 formed in the RF shield 84 are optimized based on the design of the RF coil 56 present in the system. Thus, various combinations of slits 108, 112 shown in FIGS. 2 and 5 can be implemented to minimize the eddy current, with the physical dimensions (size, shape) and locations of the slits being optimized to reduce the eddy current heating. For example, according to one embodiment, the slits 108, 112 can be staggered along the circumference/length of the RF shield 84 to further disrupt the eddy current pattern.

Beneficially, embodiments of the invention thus provide an RF shield 84 for use in an MR or hybrid PET-MR imaging system that is configured to prevent the generation of high temperature profiles on the surface of the RF shield resulting from eddy current heating. The RF shield 84 includes an arrangement of longitudinal and circumferential slits 108, 112 formed therein that disrupt eddy current profiles by disrupting any azimuthal generation of eddy current and by preventing the build-up of axial currents on the RF shield.

Therefore, according to one embodiment of the invention, an imaging apparatus includes a MRI system comprising a plurality of gradient coils positioned about a patient bore, an RF coil former comprising an inner surface and an outer surface, an RF shield positioned on the outer surface of the RF coil former so as to be formed about the RF coil former, and an RF coil positioned on the inner surface of the RF coil former and about the patient bore, with the RF coil coupled to a pulse generator to emit an RF pulse sequence and receive resulting MR signals from a subject of interest. The RF shield includes a plurality of slits formed therein configured to disrupt the formation of gradient field induced eddy currents on the RF shield.

According to another embodiment of the invention, an RF coil assembly for use in a stand-alone or hybrid MRI system includes a generally cylindrical RF coil former having an inner surface and an outer surface, an RF shield affixed to the outer surface of the RF coil former and configured to conform to the outer surface thereof, and an RF coil affixed to an inward facing surface of the RF coil former. The RF shield of the RF coil assembly further includes a plurality of longitudinal slits cut in the RF shield extending in a z-direction along the RF shield and a plurality of circumferential slits cut in the RF shield extending in a circumferential direction along the RF shield, wherein the plurality of longitudinal slits and the plurality of circumferential slits are configured to disrupt the formation of gradient field induced eddy currents on the RF shield, so as to thereby reduce a surface temperature of the RF shield.

According to yet another embodiment of the invention, a PET-MRI apparatus includes a MRI system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest. The PET-MRI apparatus also includes a positron emission tomography (PET) system having a detector array positioned to encircle the bore, with the detector array being controlled to acquire PET emissions of the subject of interest. The RF shield or the MRI system further includes a pair of raised portions formed on opposing ends of the RF shield, an indented portion formed between the pair of raised portions that is indented in the radial direction inwardly toward the patient bore, a plurality of longitudinal slits formed in the RF shield and extending in a z-direction along the RF shield, and a plurality of circumferential slits formed in the RF shield and extending in a circumferential direction along the RF shield.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A PET-MR imaging apparatus comprising:
  a magnetic resonance imaging (MRI) system comprising:
    a plurality of gradient coils positioned about a patient bore;
    an RF coil former comprising an inner surface and an outer surface, the RF coil former comprising an indented portion that is indented in a radially inward direction and a pair of raised portions positioned on opposing sides of the indented portion;
    an RF shield positioned on the outer surface of the RF coil former so as to be formed about the RF coil former, wherein the RF shield further comprises an indented portion and a pair of raised portions; and
    an RF coil positioned on the inner surface of the RF coil former and about the patient bore, with the RF coil coupled to a pulse generator to emit an RF pulse sequence and receive resulting MR signals from a subject of interest;
    wherein the RF shield includes a plurality of slits formed therein configured to disrupt the formation of gradient field induced eddy currents on the RF shield, and wherein the plurality of slits include a plurality of circumferential slits formed in a circumferential direction with respect to the RF shield, at least some one of the circumferential slits formed on one of the pair of raised portions of the RF shield and at least one of the plurality of circumferential slits formed between the indented portion of the RF shield and one of the pair of raised portions of the RF shield.

2. The PET-MR imaging apparatus of claim 1, wherein the plurality of slits further includes:
  a plurality of longitudinal slits extending in a z-direction along the RF shield.

3. The PET-MR imaging apparatus of claim 2, further comprising a heat removal device positioned on the RF shield at an end of a respective longitudinal slit to remove heat therefrom, the heat removal device comprising one or more components configured to provide electrical insulation and thermal conductivity.

4. The PET-MR imaging apparatus of claim 3, wherein the heat removal device comprises:
  an electrically insulating base plate affixed to the RF shield at the end of the respective longitudinal slit; and
  a thermally conductive plate positioned on the electrically insulating base plate.

5. The PET-MR imaging apparatus of claim 1, wherein the plurality of longitudinal slits are formed on the indented portion of the RF shield.

6. The PET-MR imaging apparatus of claim 1, wherein the plurality of longitudinal slits are formed on the pair of raised portions of the RF shield.

7. The PET-MR imaging apparatus of claim 1, further comprising a plurality of capacitive devices positioned to bridge across the plurality of circumferential slits formed between the indented portion of the RF shield and the pair of raised portions of the RF shield so as to provide an RF short.

8. The PET-MR imaging apparatus of claim 1, wherein the plurality of circumferential slits are formed on the pair of raised portions of the RF shield.

9. The PET-MR imaging apparatus of claim 1, further comprising a positron emission tomography (PET) system integrated with the MRI system, the PET system having a detector array encircling the patient bore and the RF shield with the detector array being controlled to acquire PET emissions of the subject of interest; and wherein the PET detector array is positioned in the indented portion of the RF coil former.

10. The PET-MR imaging apparatus of claim 1, wherein the plurality of slits are shaped as linear slits, teardrop-shaped slits or a combination thereof.

11. An RF coil assembly for PET-MR imaging system, the RF coil assembly comprising:
  a generally cylindrical RF coil former having an inner surface and an outer surface, the RF coil former comprising raised portions formed on opposing ends of the RF coil former and an indented portion formed between the raised portions and extending radially inward toward the inner surface;
  an RF shield affixed to the outer surface of the RF coil former and configured to conform to the outer surface thereof, the RF shield comprising raised portions and an indented portion corresponding to the raised portions and the indented portion of the RF coil former; and
  an RF coil affixed to an inward facing surface of the RF coil former;
  wherein the RF shield includes:
    a plurality of longitudinal slits cut in the RF shield extending in a z-direction along the RF shield; and
    a plurality of circumferential slits cut in the RF shield extending in a circumferential direction along the RF shield, the plurality of circumferential slits comprising at least one circumferential slit formed on one of the raised portions of the RF shield and at least one circumferential slit formed between the indented portion of the RF shield and one of the pair of raised portions of the RF shield;
  wherein the plurality of longitudinal slits and the plurality of circumferential slits are configured to disrupt the formation of gradient field induced eddy currents on the RF shield, so as to thereby reduce a surface temperature of the RF shield.

12. The RF coil assembly of claim 11, wherein the plurality of longitudinal slits comprises at least one of:
  longitudinal slits formed on the indented portion of the RF shield; and
  longitudinal slits formed on the raised portions of the RF shield.

13. The RF coil assembly of claim 11, further comprising a plurality of capacitive devices positioned to bridge across the plurality of circumferential slits cut in the RF shield.

14. The RF coil assembly of claim 11, further comprising a heat removal device positioned on the RF shield at an end of a respective longitudinal slit to remove heat therefrom.

15. The RF coil assembly of claim 14, wherein the heat removal device comprises:
- an electrically insulating base plate affixed to the RF shield at the end of the respective longitudinal slit; and
- a thermally conductive plate positioned on the electrically insulating base plate.

\* \* \* \* \*